United States Patent [19]

Ishikawa et al.

[11] 4,284,773
[45] Aug. 18, 1981

[54] 1,2,3,5-TETRAHYDROIMIDAZO-THIENOPYRIMIDIN-2-ONES

[75] Inventors: Fumiyoshi Ishikawa; Shinichiro Ashida, both of Minamifunabori, Japan

[73] Assignee: Daiichi Seiyaku Co., Ltd., Tokyo, Japan

[21] Appl. No.: 66,113

[22] Filed: Aug. 13, 1979

[30] Foreign Application Priority Data

Aug. 11, 1978 [JP] Japan .................................. 53-97832

[51] Int. Cl.³ .................. C07D 495/14; A61K 31/505
[52] U.S. Cl. .................................... 544/247; 544/250; 424/251
[58] Field of Search ................. 544/247, 250; 424/251

[56] References Cited

U.S. PATENT DOCUMENTS 3,890,321  6/1975  DeAngelis et al. ............. 544/250 X

FOREIGN PATENT DOCUMENTS 2411273  9/1975  Fed. Rep. of Germany .

OTHER PUBLICATIONS

Sauter et al., Monatsh. Chem. (1978), 109(1), 53–61.

Primary Examiner—Donald G. Daus
Assistant Examiner—Diana G. Rivers
Attorney, Agent, or Firm—Sughrue, Mion, et al.

[57] ABSTRACT

A 1,2,3,5-tetrahydroimidazothienopyrimidin-2-one represented by the formula:

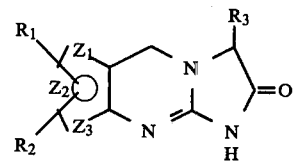

wherein one of $Z_1$, $Z_2$ and $Z_3$ is a sulfur atom and the remaining two of $Z_1$, $Z_2$ and $Z_3$ represent CH, $R_1$ and $R_2$ each represents a hydrogen atom, an alkyl group having 1 to 5 carbon atoms, a phenyl group, a chlorine atom or, when taken together $R_1$ and $R_2$ represent an alkylene chain of 3 to 5 carbon atoms, and $R_3$ represents a hydrogen atom or an alkyl group having 1 to 5 carbon atoms, and a pharmaceutically acceptable acid addition salt thereof, which exhibit an excellent blood platelet anti-aggregatory activity and are useful as anti-thrombotic agents.

6 Claims, No Drawings

1,2,3,5-TETRAHYDROIMIDAZOTHIENOPYRIMIDIN-2-ONES

BACKGROUND OF THE INVENTION

1. Field of the Invention

This invention relates to 1,2,3,5-tetrahydroimidazothienopyrimidin-2-ones represented by the formula (I):

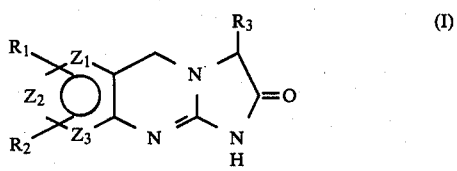

wherein one of $Z_1$, $Z_2$ and $Z_3$ is a sulfur atom and the remaining two of $Z_1$, $Z_2$ and $Z_3$ represent CH, $R_1$ and $R_2$ each represents a hydrogen atom, an alkyl group having 1 to 5 carbon atoms, a phenyl group, a chlorine atom or, when taken together $R_1$ and $R_2$ represent an alkylene chain of 3 to 5 carbon atoms, $R_3$ represents a hydrogen atom or an alkyl group having 1 to 5 carbon atoms, and the pharmaceutically acceptable acid addition salts thereof.

2. Description of the Prior Art

Hitherto, anti-thrombotic agents having an imidazopyrimidine structure have been reported in literatures. For example, W. N. Beverung et al, U.S. Pat. No. 3,932,407 discloses 1,2,3,5-tetrahydroimidazo[2,1-b]quinazolin-2-ones represented by the formula:

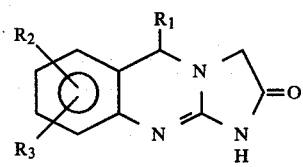

wherein $R_1$ represents a hydrogen atom or an alkyl group, and $R_2$ and $R_3$ each represents a hydrogen atom, an alkyl group or a halogen atom. However, these compounds have not proved satisfactory for clinical use in preventing thrombosis because of their side effects such as hypotensive activity.

P. Blaskiewicz et al, German Offenlegungsschrift No. 2,411,273 discloses the compounds represented by the formula:

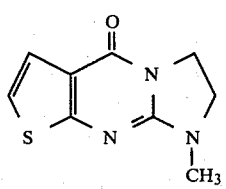

but this compound is reported as having an anti-inflammatory activity. Also, C. F. Sauter et al, Monatsh. Chem., 109, 53 (1978) discloses the compounds having the formula:

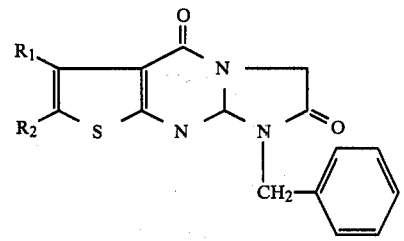

wherein $R_1$ and $R_2$ each represents —$CH_3$ or, when taken together, $R_1$ and $R_2$ represent —$CH_2CH_2CH_2CH_2$—, but blood platelet antiaggregatory activity is not reported for the above compounds.

DETAILED DESCRIPTION OF THE INVENTION

In the formula (I) above, the partial structure

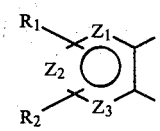

includes the following three types of condensed ring, i.e.,

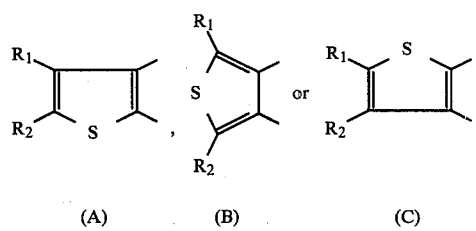

(A)   (B)   (C)

which are designated as thieno[2,3-d]pyrimidine (A), thieno[3,4-d]pyrimidine (B) or thieno[3,2-d]pyrimidine (C), respectively.

When $R_1$ and $R_2$ jointly represent an alkylene chain, the compounds of the formula (I) are tetracyclic compounds. For example, when $R_1$ and $R_2$ jointly forms a tetramethylene group $-(CH_2)_4$ in the case of thieno[2,3-d]pyrimidines (the partial structure (A) above), the compound can be represented by the formula:

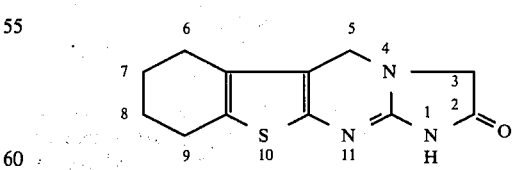

which is designated as 1,2,3,5,6,7,8,9-octahydroimidazo[1,2-a][1]benzothieno[2,3-d]pyrimidin-2-one (Compound 8, hereinafter described).

The compounds of the present invention represented by the formula (I) can exist in several possible tautomeric forms, e.g.:

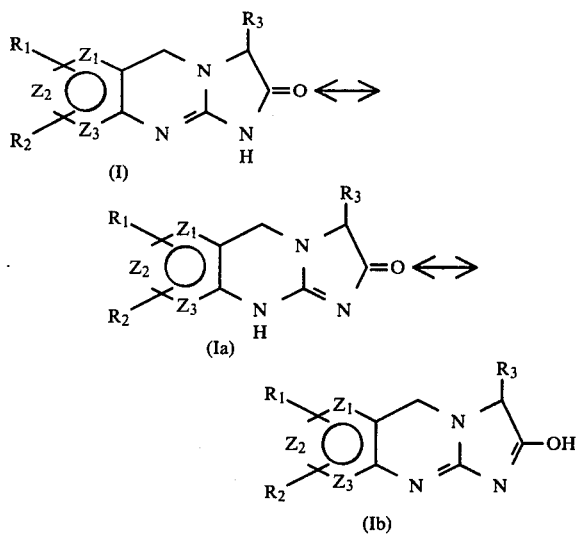

(I)

(Ia)

(Ib)

wherein $R_1$, $R_2$, $R_3$, $Z_1$, $Z_2$ and $Z_3$ are as defined above.

It should be also noted that all the possible optically active and inactive compounds are included in the scope of the compounds of the present invention represented by the formula (I) above wherein $R_3$ represents an alkyl group.

The compounds of the present invention represented by the formula (I) can be prepared according to the following reaction scheme:

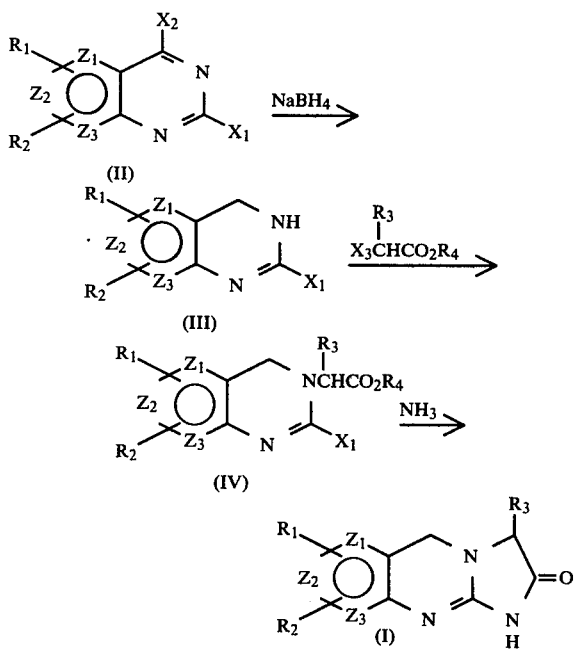

wherein $Z_1$, $Z_2$, $Z_3$, $R_1$, $R_2$ and $R_3$ are as defined above, and $X_1$, $X_2$ and $X_3$ each represents a chlorine atom or a bromine atom and $R_4$ represents a lower alkyl group.

As seen in the above reaction scheme, a 2,4-dihalothienopyrimidine having the formula (II) is reduced with an alkali metal borohydride such as sodium borohydride, lithium borohydride and the like, preferably with sodium borohydride, in an inert organic solvent such as methanol, ethanol, chloroform, aqueous tetrahydrofuran or a mixture thereof at a temperature of about 25° to about 100° C. for about one hour to overnight (about 16 hours) to give a 2-halo-3,4-dihydrothienopyrimidine represented by the formula (III) in high yield. The resulting compound of the formula (III) is then reacted with an α-haloalkanoic acid alkyl ester, e.g., ethyl bromoacetate, ethyl α-bromopropionate and the like, in an inert organic solvent such as acetone, methyl ethyl ketone and the like in the presence of an acid acceptor such as powdered potassium carbonate or sodium carbonate in an inert gas atmosphere, i.e., nitrogen or argon, while heating at a temperature of about 25° C. to about 100° C., preferably at refluxing temperature, with vigorous stirring for a period of about 1 to about 48 hours to give a 2-halo-3-α-alkoxycarbonylalkyl-3,4-dihydrothienopyrimidine represented by the formula (IV). The resulting compound (IV) is then heated with ammonia in an alcohol such as methanol or ethanol at a temperature of about 100° to about 150° C., preferably 120° C. to 130° C., for about 2 to about 16 hours in a sealed tube filled with an inert gas, e.g., nitrogen or argon, to obtain the desired compound of the formula (I).

The pharmaceutically acceptable acid addition salts of the compounds represented by the formula (I) can be easily prepared by adding a selected nontoxic acid to a methanolic solution of the compound (I). Suitable examples of pharmaceutically acceptable nontoxic acid addition salts are hydrochloride, hydrobromide, alkyl- or arylsulfonate, phosphate, sulfate, fumarate, maleate, succinate, tartarate, citrate and other non-toxic acid salts which are commonly used in the art.

The synthesis of the compounds of the present invention is further illustrated by the following Synthesis Examples. Unless otherwise indicated, all parts, percents, ratios and the like are by weight.

SYNTHESIS EXAMPLE 1

Preparation of 2-chloro-5,6-dimethyl-3,4-dihydrothieno[2,3-d]pyrimidine (Compound 1A of Formula III)

To a solution of 4.66 g of 2,4-dichloro-5,6-dimethylthieno[2,3-d]pyrimidine in 150 ml of ethanol-chloroform (1:1 by volume) was slowly added 2.32 g of sodium borohydride with stirring. The mixture was stirred at room temperature for 6 hours and the solvent removed in vacuo. To the solid residue was added 50 ml of water and the insoluble material was filtered, washed with water, dried, and recrystallized from benzene to give 2.05 g of 2-chloro-5,6-dimethyl-3,4-dihydrothieno[2,3-d]pyrimidine, mp 170°–172° C.

Elemental Analysis:

Calc'd for $C_8H_9ClN_2S$: C, 47.88; H, 4.52; N, 13.96; Found: C, 47.73; H, 4.47; N, 13.88.

SYNTHESIS EXAMPLE 2

In the same manner as described in Example 1 but using an equimolar amount of a substituted 2,4-dichlorothienopyrimidine having the formula (II) in place of the 2,4-dichloro-5,6-dimethylthieno[2,3-d]pyrimidine used in Example 1, the following substituted 2-halo-3,4-dihydrothienopyrimidine compounds (Compounds 2A to 17A) having the formula (III) were produced. In this example, the reaction was carried out at a temperature of 40° to 50° C. for Compounds 5A, 7A, 8A, 15A and 17A, at a temperature of 50° to 60° C. for Compound 9A, at a temperature of 40°–45° C. for Compound 16A and at room temperature for the remaining compounds.

tube at 120°–130° C. in an oil bath for 5 hours. After cooling, the precipitated crystals were filtered, washed

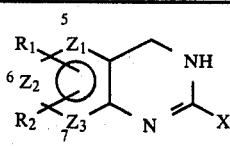

(III)

| Compound No. | $Z_1$ | $Z_2$ | $Z_3$ | $X_1$ | $R_1$ | $R_2$ | mp (°C.)* |
|---|---|---|---|---|---|---|---|
| 2A | CH | CH | S | Cl | 5-H | 6-H | 146–148 (dec) |
| 3A | CH | CH | S | Cl | 5-H | 6-CH$_3$ | 130–140[195–200(dec.)] |
| 4A | CH | CH | S | Cl | 5-CH$_3$ | 6-H | 156–159 (dec) |
| 5A | CH | CH | S | Cl | 5-Cl | 6-CH$_3$ | 172–174 (dec) |
| 6A | CH | CH | S | Cl | 5-CH$_3$ | 6-Cl | 140–160[227–230(dec.)] |
| 7A | CH | CH | S | Cl | —(CH$_2$)$_3$— | | 151–153 (dec) |
| 8A | CH | CH | S | Cl | —(CH$_2$)$_4$— | | 140–142 (dec) |
| 9A | CH | CH | S | Cl | —(CH$_2$)$_5$— | | 143–145 (dec) |
| 10A | CH | CH | S | Cl | 5-C$_6$H$_5$ | 6-H | 147–148 (dec) |
| 11A | S | CH | CH | Cl | 6-H | 7-H | 138–140 (dec) |
| 12A | S | CH | CH | Cl | 6-CH$_3$ | 7-H | 120–125[158–166(dec.)] |
| 13A | CH | S | CH | Cl | 5-H | 7-H | 151–153 |
| 14A | CH | S | CH | Cl | 5-CH$_3$ | 7-H | 168–171 |
| 15A | CH | CH | S | Cl | 5-C$_3$H$_7$ | 6-C$_2$H$_5$ | unclear |
| 16A | CH | CH | S | Cl | 5-CH$_3$ | 6-C$_3$H$_7$ | unclear |
| 17A | CH | CH | S | Cl | 5-CH$_3$ | 6-C$_5$H$_{11}$ | unclear |

*Generally, these compounds do not give clear melting or decomposing point because of the instability under heating. That is, upon heating these compounds gradually become wet and then solidified followed by decomposition. The figure in bracket [ ] means the decomposing point after the solidification.

SYNTHESIS EXAMPLE 3

Preparation of 6,7-dimethyl-1,2,3,5-tetrahydroimidazo[1,2-a]thieno[2,3-d]pyrimidine-2-one (Compound 1 of Formula I)

A mixture of 6.0 g of 2-chloro-5,6-dimethyl-3,4-dihydrothieno[2,3-d]pyrimidine, 5.52 g of ethyl bromoacetate and 12.5 g of powdered potassium carbonate in 300 ml of methyl ethyl ketone was heat-refluxed with stirring under a nitrogen atmosphere for 4 hours. After cooling, an insoluble inorganic salt was filtered off and the filtrate was concentrated in vacuo to give a crude oil of 2-chloro-3-ethoxycarbonylmethyl-5,6-dimethyl-3,4-dihydrothieno[2,3-d]pyrimidine. Because of the instability of the resulting compound, the crude oil was used in the subsequent reaction.

A mixture of the crude oil obtained above in 50 ml of 10% ammonia-ethanol solution was heated in a sealed tube at 120°–130° C. in an oil bath for 5 hours. After cooling, the precipitated crystals were filtered, washed with water and dried to give 3.0 g of 6,7-dimethyl-1,2,3,5-tetrahydroimidazo[1,2-a]thieno[2,3-d]pyrimidin-2-one. The hydrochloride salt of the resulting compound was prepared by reacting the free compound with hydrochloric acid in methanol in a usual manner and had a melting point of 249°–255° C. (with decomposition).

Elemental Analysis:
Calc'd for C$_{10}$H$_{12}$ClN$_3$O: C, 46.60; H, 4.69; N, 16.30; Found: C, 46.66; H, 4.61; N, 16.29.

SYNTHESIS EXAMPLE 4

In the same manner as described in Example 3 but using an equimolar amount of a substituted 2-halo-3,4-dihydrothienopyrimidine prepared in Example 2 in place of the 2-chloro-5,6-dimethyl-3,4-dihydrothieno[2,3-d]pyrimidine (1A) used in Example 3, the following compounds (Compounds 2 to 17) of the formula (I) were obtained.

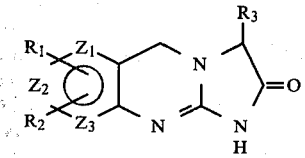

| Comp. No. | $Z_1$ | $Z_2$ | $Z_3$ | $R_1$ | $R_2$ | $R_3$ | Melting* Point (°C.) | Empirical Formula | Elemental Analysis Found Values (calc'd values in bracket) | | |
|---|---|---|---|---|---|---|---|---|---|---|---|
| | | | | | | | | | C | H | N |
| 2 | CH | CH | S | 6-H | 7-H | H | 200 (dec.) | C$_8$H$_8$ClN$_3$OS | 41.62 (41.83) | 3.42 (3.51) | 18.55 (18.30) |
| 3 | CH | CH | S | 6-H | 7-CH$_3$ | H | 233–235 (dec.) | C$_9$H$_{10}$ClN$_3$OS | 44.17 (44.35) | 4.08 (4.14) | 17.39 (17.24) |
| 4 | CH | CH | S | 6-CH$_3$ | 7-H | H | 252–257 (dec.) | C$_9$H$_{10}$ClN$_3$OS . ½ H$_2$O | 42.69 (42.78) | 3.98 (4.38) | 16.77 (16.63) |
| 5 | CH | CH | S | 6-Cl | 7-CH$_3$ | H | 241–243 (dec.) | C$_9$H$_9$Cl$_2$N$_3$OS . ½ H$_2$O | 37.38 (37.64) | 3.47 (3.51) | 14.69 (14.63) |
| 6 | CH | CH | S | 6-CH$_3$ | 7-Cl | H | 220– (dec.) | C$_9$H$_9$Cl$_2$N$_3$OS | 39.16 (38.86) | 3.47 (3.26) | 15.12 (15.11) |
| 7 | CH | CH | S | —(CH$_2$)$_3$— | | H | 250– (dec.) | C$_{11}$H$_{12}$ClN$_3$OS | 49.11 (48.98) | 3.86 (4.49) | 15.87 (15.58) |

-continued

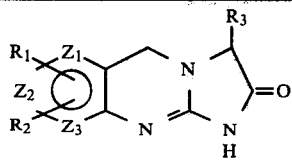

| Comp. No. | $Z_1$ | $Z_2$ | $Z_3$ | $R_1$ | $R_2$ | $R_3$ | Melting* Point (°C.) | Empirical Formula | Elemental Analysis Found Values (calc'd values in bracket) | | |
|---|---|---|---|---|---|---|---|---|---|---|---|
| | | | | | | | | | C | H | N |
| 8 | CH | CH | S | —(CH$_2$)$_4$— | | H | 257–259 (dec.) | $C_{12}H_{14}ClN_3OS$ | 50.87 (50.79 | 4.93 4.97 | 14.93 14.81) |
| 9 | CH | CH | S | —(CH$_2$)$_5$— | | H | 132–138 (dec.) | $C_{14}H_{16}ClN_3OS$ | 52.43 (52.43 | 5.35 5.42 | 14.38 14.11) |
| 10 | CH | CH | S | 6-C$_6$H$_5$ | 7-H | H | 233–234 (dec.) | $C_{14}H_{12}ClN_3OS$ | 54.79 (55.00 | 4.22 3.96 | 14.02 13.74) |
| 11 | S | CH | CH | 7-H | 8-H | H | >280 | $C_8H_8ClN_3OS$ | 42.20 (41.83 | 3.48 3.51 | 18.67 18.30) |
| 12 | S | CH | CH | 7-CH$_3$ | 8-H | H | >280 | $C_9H_{10}ClN_3OS$ | 44.10 (44.35 | 4.46 4.14 | 17.12 17.24) |
| 13 | CH | S | CH | 6-H | 8-H | H | 262–264 (dec.) | $C_8H_8ClN_3OS$ | 41.70 (41.83 | 3.47 3.51 | 18.50 18.30) |
| 14 | CH | S | CH | 6-CH$_3$ | 8-H | H | >280 | $C_9H_{10}ClN_3OS$ | 44.49 (44.35 | 4.17 4.14 | 17.74 17.24) |
| 15 | CH | CH | S | 6-C$_3$H$_7$ | 7-C$_2$H$_5$ | H | 214–216 (dec.) | $C_{13}H_{18}ClN_3OS$ | 51.67 (52.08 | 5.96 6.05 | 14.03 14.02) |
| 16 | CH | CH | S | 6-CH$_3$ | 7-C$_3$H$_7$ | H | 209–212 (dec.) | $C_{12}H_{16}ClN_3OS$ | 50.88 (50.43 | 5.69 5.64 | 14.51 14.70) |
| 17 | CH | CH | S | 6-CH$_3$ | 7-C$_5$H$_{11}$ | H | 206–208 (dec.) | $C_{14}H_{20}ClN_3OS$ | 53.39 (53.58 | 6.30 6.42 | 13.63 13.39) |
| 18 | CH | CH | S | —(CH$_2$)$_3$— | | CH$_3$ | 240–245 (dec.) | $C_{13}H_{15}ClN_3OS$ | 52.43 (52.24 | 5.42 5.51 | 14.11 14.02) |
| 19 | CH | CH | S | —(CH$_2$)$_3$— | | C$_2$H$_5$ | 220–225 (dec.) | $C_{14}H_{17}ClN_3OS$ | 53.92 (53.81 | 5.82 5.91 | 13.48 13.24) |

*Melting Point of Hydrochloride

The infrared absorption spectrum and the nuclear magnetic resonance spectrum of all the compounds were found to be consistent with the chemical structure.

The compounds of the present invention have unique properties as blood platelet anti-aggregatory agents. These compounds are useful in the prevention of intravascular thrombosis, prevention of coronary thrombosis, prevention of transient ischemic episodes, prevention of platelet thrombosis in the use of prosthetic devices (artificial heart valves, etc.) and other thrombotic complications including thromboangitis obliterans, etc.

As stated as background of the present invention, optionally substituted imidazo[2,1-b]quinazolines reported by Beverung et al have a potent hypotensive activity which is undesirable side effect for anticlotting therapy. On the other hand, the compounds of the present invention do not have a hypotensive activity and more potent blood platelet antiaggregatory activity than imidazo[2,1-b]quinazolines.

EXAMPLE

The aggregometer method of Born [G. V. Born, Nature, 194, 927 (1962)] was used to assess the in vitro activity of the various compounds as to inhibition of adenosine diphosphate (ADP) and collagen (Coll) induced platelet aggregation. Platelet rich plasma (PRP) was separated by centrifugation from citrated (0.313%) rat blood.

A methanolic solution of the test compound was added to the PRP, then aggregation was induced by adding to the mixture of ADP solution containing CaCl$_2$ or a collagen suspension prepared according to the method described by Ashida et al [S. Ashida and Y. Abiko, Thromb. Diath. Haemorrh., 30, 528 (1975)], and the optical density of the resulting mixture was determined. Control was made by addition of methanol instead of the above methanolic solution of the test compound, and the optical density of the resulting mixture was also determined, which showed 100% aggregation. A dose response curve was drawn from the results obtained above and the effective concentration giving a 50% inhibition (EC$_{50}$) was calculated.

The blood pressure of normal rat was measured at 5–6 hours after the oral administration at a dose of 50 mg/kg.

The most preferred compound, 6-methyl-1,2,3,5-tetrahydroimidazo[2,1-b]quinazolin-2-one (BL-3459) reported by Beverung et al, was tested for the biological activities at the same time. Table I is illustrative of the blood platelet anti-aggregatory and hypotensive activities of some of the preferred embodiments of the present invention and BL-3459.

TABLE I

| Compound No. | Inhibition of Platelet Aggregation | | | Blood Pressure % Reduction at 50 mg/kg(p.o) in rat |
|---|---|---|---|---|
| | in vitro (EC$_{50}$) | | ex vivo* % Inhibition at 50 mg/kg(p.o) in rat | |
| | Coll (μM) | ADP (μM) | | |
| 1 | 1 | 5 | 84 | 5 ± 3 |
| 4 | 15 | 19 | | |
| 6 | 1.9 | 4.2 | 24 | |
| 8 | 0.1 | 5 | 57 | 8 ± 2 |

TABLE I-continued

| Compound No. | Inhibition of Platelet Aggregation | | ex vivo* % Inhibition at 50 mg/kg(p.o)in rat | Blood Pressure % Reduction at 50 mg/kg(p.o)in rat |
|---|---|---|---|---|
| | in vitro ($EC_{50}$) | | | |
| | Coll ($\mu M$) | ADP ($\mu M$) | | |
| 9 | 15 | 20 | | |
| 11 | 10 | 85 | | |
| 14 | 3.5 | 17 | 32 | |
| 15 | 2.2 | 3 | 90 | |
| 16 | 0.08 | 0.58 | 60 | |
| 17 | 0.19 | 2 | | |
| 18 | 0.60 | 48 | | |
| BL-3459 0.8 | 5 | 57 | 35 + 3 | |

*ex vivo:
Blood samples were collected 2 hours after oral administration of the compound to be tested or vehicle alone. Platelet rich plasmas were obtained by centrifugation of the blood. Platelet aggregation was induced by adding collagen suspension to the platelet rich plasma and was compared with that observed with the platelet rich plasma from the control rats given vehicle alone.

A suitable dosage level for oral administration can range from about 0.5 to about 30 mg/kg in single or multiple doses along with an appropriate pharmaceutically acceptable carrier and diluent in the form of a tablet, a capsule or powder, if desired. The preferred dosage level of the compounds of the invention for adult human is in the range of about 10 to about 200 mg/day.

While the invention has been described in detail and with reference to specific embodiments thereof, it will be apparent to one skilled in the art that various changes and modifications can be made therein without departing from the spirit and scope thereof.

What is claimed is:

1. A compound represented by the formula:

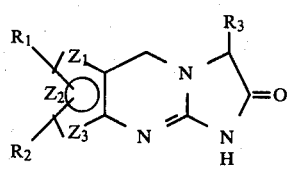

wherein one of $Z_1, Z_2$ and $Z_3$ is a sulfur atom and the remaining two of $Z_1, Z_2$ and $Z_3$ represent CH, $R_1$ and $R_2$ each represents a hydrogen atom, an alkyl group having 1 to 5 carbon atoms, a phenyl group, or a chlorine atom or, when $Z_1$ or $Z_3$ is a sulfur atom, $R_1$ and $R_2$ taken together can represent an alkylene chain of 3 to 5 carbon atoms, and $R_3$ represents a hydrogen atom or an alkyl group having 1 to 5 carbon atoms, and a pharmaceutically acceptable acid addition salt thereof.

2. A compound represented by the formula:

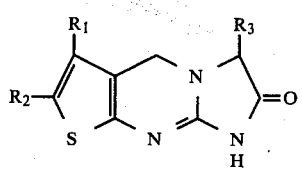

wherein $R_1$ and $R_2$ each represents a hydrogen atom, an alkyl group having 1 to 5 carbon atoms, a phenyl group, a chlorine atom or, when taken together, $R_1$ and $R_2$ represent an alkylene chain of 3 to 5 carbon atoms, and $R_3$ represents a hydrogen atom or an alkyl group having 1 to 5 carbon atoms, and a pharmaceutically acceptable acid addition salt thereof.

3. A compound represented by the formula:

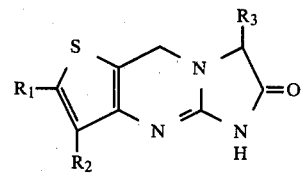

wherein $R_1$ and $R_2$ each represents a hydrogen atom, an alkyl group or, when taken together, $R_1$ and $R_2$ represent an alkylene chain of 3 to 5 carbon atoms, and $R_3$ represents a hydrogen atom or an alkyl group having 1 to 5 carbon atoms, and a pharmaceutically acceptable acid addition salt thereof.

4. A compound represented by the formula:

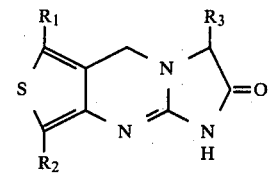

wherein $R_1$ and $R_2$ each represents a hydrogen atom or an alkyl group, and $R_3$ represents a hydrogen atom or an alkyl group having 1 to 5 carbon atoms, and a pharmaceutically acceptable acid addition salt thereof.

5. The compound of claim 2, wherein $R_1$ and $R_2$ jointly represent a tetramethylene group ($-CH_2CH_2CH_2CH_2-$), $R_3$ is a hydrogen atom and the salt is hydrochloride.

6. The compound of claim 2, wherein $R_1$ and $R_2$ each represents a methyl group and the salt is hydrochloride.

* * * * *